(12) United States Patent
Krzysik et al.

(10) Patent No.: US 6,187,695 B1
(45) Date of Patent: *Feb. 13, 2001

(54) COOL FEELING TISSUE PRODUCT AND METHOD

(75) Inventors: Duane G. Krzysik, Appleton; Cynthia W. Henderson, Neenah; Lorrie L. Krynock, Appleton, all of WI (US)

(73) Assignee: Kimberly-Clark Worldwide, Inc., Neenah, WI (US)

( * ) Notice: Under 35 U.S.C. 154(b), the term of this patent shall be extended for 0 days.

This patent is subject to a terminal disclaimer.

(21) Appl. No.: 09/207,744

(22) Filed: Dec. 8, 1998

(51) Int. Cl.[7] .................................................. A61K 31/695
(52) U.S. Cl. ........................ 442/62; 442/98; 442/99; 442/100; 442/97; 427/286; 427/288
(58) Field of Search ............................. 442/62, 97, 98, 442/99, 100; 427/286, 288

(56) References Cited

U.S. PATENT DOCUMENTS

| | | |
|---|---|---|
| 1,687,625 | 10/1928 | MacKenzie . |
| 3,896,807 | 7/1975 | Buchalter . |
| 4,020,153 | 4/1977 | Rowsell et al. . |
| 4,069,345 | 1/1978 | Gascoyne et al. . |
| 4,070,449 | 1/1978 | Rowsell et al. . |
| 4,190,643 | 2/1980 | Watson et al. . |
| 4,292,028 | 9/1981 | Barr . |
| 4,318,900 | 3/1982 | Rowsell et al. . |
| 4,904,524 | 2/1990 | Yoh . |
| 5,059,282 | 10/1991 | Ampulski et al. . |
| 5,122,519 * | 6/1992 | Ritter .................................. 514/152 |
| 5,160,739 | 11/1992 | Kanga . |
| 5,208,013 | 5/1993 | Klein . |
| 5,223,096 | 6/1993 | Phan et al. . |
| 5,254,331 | 10/1993 | Mausner . |
| 5,302,382 | 4/1994 | Kasprzak . |
| 5,326,557 | 7/1994 | Glover et al. . |
| 5,380,527 | 1/1995 | Legrow et al. . |
| 5,397,564 | 3/1995 | Seki et al. . |
| 5,397,566 | 3/1995 | Thimineur et al. . |
| 5,411,734 | 5/1995 | Vargas et al. . |
| 5,439,682 | 8/1995 | Wivell et al. . |
| 5,449,512 | 9/1995 | Simmons . |
| 5,451,404 | 9/1995 | Furman . |
| 5,480,637 | 1/1996 | Smith . |
| 5,525,344 | 6/1996 | Wivell . |
| 5,525,346 | 6/1996 | Hartung et al. . |
| 5,538,595 | 7/1996 | Trokhan et al. . |
| 5,556,630 | 9/1996 | Znaiden et al. . |
| 5,567,427 | 10/1996 | Papadakis . |
| 5,575,891 | 11/1996 | Trokhan et al. . |
| 5,597,577 | 1/1997 | Mathewson . |
| 5,599,549 | 2/1997 | Wivell et al. . |
| 5,614,293 * | 3/1997 | Krzysik et al. ...................... 428/211 |
| 5,650,218 * | 7/1997 | Krzysik et al. ...................... 428/195 |
| 5,665,426 * | 9/1997 | Krzysik et al. ...................... 427/211 |
| 5,885,697 * | 3/1999 | Krzysik et al. ...................... 428/211 |

* cited by examiner

*Primary Examiner*—Elizabeth M. Cole
(74) *Attorney, Agent, or Firm*—Gregory E. Croft

(57) ABSTRACT

A tissue product is disclosed which provides a cooling feeling when in contact with skin. A suitable implementation includes a soft uncreped throughdried tissue product having generally uniformly distributed surface deposits of a chemical composition that contains an oil, a wax, and preferably a fatty alcohol. Suitable compositions include those which have a melting point of from about 30° C. to about 70° C. and which are applied to the outer surfaces of the tissue product in melted form.

36 Claims, No Drawings

COOL FEELING TISSUE PRODUCT AND METHOD

TECHNICAL FIELD

This invention relates generally to a cool feeling tissue product and method of preparing the tissue product. More particularly, the invention relates to a tissue product including a lotion composition applied to a surface of the tissue, the lotion providing a cool sensation when in contact with skin.

BACKGROUND

Disposable tissues, such as facial and bathroom tissues and wipes, are commonly made of cellulose or cellulosic webs. These tissues come in contact with skin when used, and are preferably soft and comfortable to the touch. Various techniques are known in the art to improve the comfort and touch of tissues, including the selection of the source pulp for the cellulose web, manufacturing methods that minimize compression and pressure on the web, and addition of compositions to soften the tissue, such as lotions.

While it is known to provide tissues with lotions to improve comfort, the addition of lotions can decrease the thickness of the tissue sheets due to a partial collapse of the web structure when exposed to moisture and processing pressures. Recently, improved tissues containing a lotion and methods of making tissues containing a lotion were patented as U.S. Pat. Nos. 5,601,871; 5,614,293; and 5,650,218 to Krzysik et al.. The improved tissues and methods use uniformly distributed deposits on the surface of a soft uncreped throughdried tissue. These methods result in improved tissues having advantages for use as facial and bathroom tissues. The improved tissues impart benefits to the user, including superior softness. The patents identified above indicate a number of compositions useful for applying to the tissue, and these compositions provide a softer and more comfortable tissue.

While the tissues and methods patented by Krzysik et al. provide advantages over preexisting tissues, improvements that make the tissues more comfortable or impart a beneficial attribute in specific uses remain desirable.

SUMMARY OF THE INVENTION

The present invention is directed to a tissue product including a cooling composition added to exterior surfaces of the tissue which feels cool when applied to the skin. The invention is also directed to a method of making a tissue product having a "cooling" composition, as well as to the "cooling" composition itself. The tissue product includes a tissue web onto which a lotion composition is applied. The tissue containing the lotion composition provides a cooling sensation when in contact with human skin.

In one implementation of the present invention, the cooling composition includes a silicone oil consisting of a methylated linear siloxane polymer mixture, end capped with trimethyl siloxyl units (dimethicone), a $C_{1-18}$ alkyl fatty acid ester, such a isopropyl palmitate, a purified mineral oil, a fatty acid or fatty alcohol ethoxylate (1 to 200 moles EO) ceteareth-20, and cetyl alcohol. In another embodiment, the lotion composition includes dimethicone, mineral oil, a mixture of cetyl acetate and acetylated lanolin alcohol, tridecyl neopentanoate, tocopherol, and cerasin wax. The lotion composition is heated to a temperature above the melting point of the composition, causing it to melt. This melted composition is then applied to one or both sides of the tissue web. In specific implementations, the composition is applied at a density from about 100 to about 1,000,000 deposits per square inch of the tissue web. Following deposition of the melted lotion composition, the composition is resolidified to provide an improved tissue product.

When in contact with human skin, the improved tissue product provides a cooling sensation that is not experienced with most other lotion compositions. This cooling sensation provides a pleasant feel to the skin, and is an improvement over prior tissue products.

The above summary of the present invention is not intended to describe each illustrated embodiment of the present invention. The detailed description which follows should make more aspects of the invention apparent.

DETAILED DESCRIPTION OF THE INVENTION

A superior tissue can be made by applying, on the surface(s) of a tissue, large numbers of individual deposits of a melted lotion composition, and thereafter resolidifying the composition to form a uniform distribution of solid deposits on the surface(s) of the tissue. The lotion composition provides a cooling sensation when in contact with human skin. The composition is a solid at room temperature and rapidly solidifies after deposition, and therefore it has less tendency to penetrate and migrate into the sheet. Compared to tissues with liquid formulations, this leaves a greater percentage of the added composition on the surface of the sheet, where it can contact and transfer to the user's skin to provide a cooling sensation and other benefits. Furthermore, the efficient placement of the composition at the surface of the sheet allows a lower amount of the composition to be used to deliver the same benefit.

The cooling composition includes a silicone oil consisting of a methylated linear siloxane polymer mixture, end capped with trimethyl siloxyl units (dimethicone), a $C_{1-18}$ alkyl fatty acid ester, a purifued mineral oil, a fatty acid or fatty alcohol or an ehoxylate thereof said ethoxylatehaving 1 to 200 moles EO. In a specific implementation, the lotion composition includes about 1 to 5 parts by weight dimethicone, about 2 to 10 parts by weight isopropyl palmitate, about 25 to 35 parts by weight mineral oil, about 30 to 40 parts by weight ceteareth-20, and about 15 to 20 parts by weight cetyl alcohol. In another implementation, the lotion composition includes about 20 to 40 parts by weight dimethicone, about 15 to 35 parts by weight mineral oil, about 5 to 15 parts by weight of a mixture of cetyl acetate and acetylated lanolin alcohol, about 15 to 25 parts by weight tridecyl neopentanoate, and about 10 to 30 parts by weight cerasin wax.

The lotion composition is heated to a temperature above the melting point of the composition, causing the composition to melt. The lotion composition is heated to a temperature of about 2° C. to about 5° C. above the melting point of the composition in certain implementations. After melting, the composition is applied to one or both sides of a tissue web. The composition subsequently cools and hardens. The tissue web may be cooled before or after the deposits of the coating composition are applied in order to accelerate solidification of the deposits. The tissue product made with the lotion composition provides a cooling sensation when in contact with human skin.

In certain implementations, the lotion composition has a melting point from about 30° C. to about 70° C. While various cellulose webs may be used, in a specific implementation the web is an uncreped throughdried tissue. The amount of the lotion composition applied to the tissue is from about 5 to about 25 weight percent based on the weight of the tissue in one implementation, and from about 10 to about 15 weight percent based on the weight of the tissue in another implementation.

The composition may specifically comprise about 2 parts by weight dimethicone, about 4 parts by weight isopropyl palmitate, about 34 parts by weight mineral oil, about 35 parts by weight ceteareth-20, and about 20 parts by weight cetyl alcohol. Another implementation comprises about 30 parts by weight dimethicone, about 25 parts by weight mineral oil, about 10 parts by weight of a mixture of cetyl acetate and acetylated lanolin alcohol, about 20 parts by weight tridecyl neopentanoate, about 5 parts by weight tocopherol, and about 20 parts by weight cerasin wax.

A preferred method to uniformly apply the heated composition to the surface of the tissue web is rotogravure printing, either direct or indirect (offset), because it is the most exact printing process and offers maximum control of the composition distribution and transfer rate. However, other printing methods, such as flexographic printing, can also be used.

The surface area coverage of the composition is preferably uniform over substantially all of the tissue surface, but only partially covers the surface(s) of the tissue product. This is achieved by a large number of small deposits which, when viewed by the naked eye, appear to cover the entire surface of the tissue. The actual surface area coverage of the deposits can be from about 30 to about 100 percent, more specifically from about 50 to about 80 percent. By providing a large number of very small deposits, the penetration of the composition can be more easily controlled to substantially remain on or near the surface of the tissue. Gravure printing is ideally suited to such an application by providing, for example, from about 10 to about 1000 deposits per lineal inch of surface, or from about 100 to about 1,000,000 deposits per square inch. This encompasses several well known engraving techniques, such as mechanical engraving, acid-etch engraving, electronic engraving and ceramic laser engraving.

A suitable electronic engraved example is about 250 deposits per lineal inch of surface, or about 62,500 deposits per square inch. By providing such a large number of small deposits, the uniformity of the deposit distribution is very high. Also, because the large number of small deposits are applied to the surface of the tissue, the deposits more readily resolidify on the surface of the tissue, where they are most effective in benefiting the user. As a consequence, a relatively low amount of the composition can be used to cover a large area.

While the present invention has been described with reference to several particular implementations, those skilled in the art will recognize that many changes may be made hereto without departing from the spirit and scope of the present invention. It is intended that the specification and examples be considered as exemplary only, with the true scope and spirit of the invention being indicated by the following claims.

We claim:

1. A method of making a tissue product comprising:

(a) providing a lotion composition comprising
       about 0.1 to 5 parts by weight of a silicone oil,
       about 0.2 to 10 parts by weight of a $C_{1-18}$ alkyl ester of a fatty acid,
       about 0.25 to 35 parts by weight purified mineral oil,
       about 30 to 40 parts by weight fatty alcohol ethoxylate or fatty acid ethoxylate having 1 to 200 moles EO, and
       about 15 to 20 parts by weight of a fatty alcohol;

(b) heating the lotion composition of (a) to a temperature above the melting point of the composition, causing the composition to melt;

(c) applying from about 100 to about 1,000,000 deposits of the melted lotion composition per square inch to one or both sides of a tissue web; and (d) resolidifying the deposits of the melted lotion composition.

2. A method of making a tissue product comprising:

(a) providing a lotion composition comprising
       about 0.1 to 5 parts by weight dimethicone,
       about 0.2 to 10 parts by weight isopropyl palmitate,
       about 0.25 to 35 parts by weight mineral oil,
       about 30 to 40 parts by weight ceteareth-20, and
       about 15 to 20 parts by weight cetyl alcohol;

(b) heating the lotion composition of (a) to a temperature above the melting point of the composition, causing the composition to melt;

(c) applying from about 100 to about 1,000,000 deposits of the melted lotion composition per square inch to one or both sides of a tissue web; and (d) resolidifying the deposits of the melted lotion composition.

3. The method according to claim 1, wherein the tissue product provides a cooling sensation when in contact with human skin.

4. The method according to claim 1, wherein the lotion composition has a melting point of from about 30° C. to about 70° C.

5. The method according to claim 1, wherein the tissue product is an uncreped throughdried tissue.

6. The method according to claim 1, wherein the heated lotion composition is applied to the tissue with a rotogravure printer.

7. The method according to claim 1, wherein from about 25 to about 100 percent of the surface area of the tissue is covered with the lotion composition.

8. The method according to claim 1, wherein the amount of the lotion composition applied to the tissue is from about 5 to about 25 weight percent based on the weight of the tissue.

9. The method according to claim 1, wherein the amount of the lotion composition applied to the tissue is from about 10 to about 15 weight percent based on the weight of the tissue.

10. The method according to claim 1, wherein the lotion composition is heated to a temperature of about 2° C. to about 5° C. above the melting point of the composition.

11. The method according to claim 1, wherein the tissue web is cooled before or after the deposits of the coating composition are applied in order to accelerate solidification of the deposits.

12. A method of making a tissue product comprising:

(a) providing a lotion composition comprising
       about 20 to 40 parts by weight dimethicone,
       about 15 to 35 parts by weight mineral oil,
       about 5 to 15 parts by weight of a mixture of cetyl acetate and acetylated lanolin alcohol,
       about 15 to 25 parts by weight tridecyl neopentanoate, and
       about 10 to 30 parts by weight cerasin wax;

(b) heating the lotion composition of (a) to a temperature above the melting point of the composition, causing the composition to melt;

(c) applying from about 100 to about 1,000,000 deposits of the melted lotion composition per square inch to one or both sides of a tissue web; and (d) resolidifying the deposits of the melted lotion composition.

13. The method according to claim 12, wherein the tissue product provides a cooling sensation when in contact with skin.

14. The method according to claim 12, wherein the lotion composition has a melting point of from about 30° C. to about 70° C.

15. The method according to claim 12, wherein the tissue product is an uncreped throughdried tissue.

16. The method according to claim 12, wherein the heated lotion composition is applied to the tissue with a rotogravure printer.

17. The method according to claim 12, wherein from about 25 to about 100 percent of the surface area of the tissue product is covered with the composition.

18. The method according to claim 12, wherein the amount of the lotion composition applied to the tissue is from about 5 to about 25 weight percent based on the weight of the tissue.

19. The method according to claim 12, wherein the amount of the lotion composition applied to the tissue is from about 10 to about 15 weight percent based on the weight of the tissue.

20. The method according to claim 12, wherein the composition is heated to a temperature of about 2° C. to about 5° C. above the melting point of the composition.

21. The method according to claim 12, wherein the tissue web is cooled before or after the deposits of the coating composition are applied in order to accelerate solidification of the deposits.

22. A method of making a tissue product comprising:
(a) providing a composition comprising
about 2 parts by weight dimethicone,
about 4 parts by weight isopropyl palmitate,
about 34 parts by weight mineral oil,
about 35 parts by weight ceteareth-20, and
about 20 parts by weight cetyl alcohol;

(b) heating the composition of (a) to a temperature above the melting point of the composition, causing the composition to melt;

(c) applying from about 100 to about 1,000,000 deposits of the melted composition per square inch to one or both sides of a tissue web; and (d) resolidifying the deposits of the melted composition.

23. The method according to claim 22, wherein the tissue product provides a cooling sensation when in contact with skin.

24. The method according to claim 22, wherein the composition has a melting temperature of from about 30° C. to about 70° C.

25. A method of making a tissue product comprising:
(a) providing a composition comprising
about 30 parts by weight dimethicone,
about 25 parts by weight mineral oil,
about 10 parts by weight of a mixture of cetyl acetate and acetylated lanolin alcohol,
about 20 parts by weight tridecyl neopentanoate,
about 5 parts by weight tocopherol, and
about 20 parts by weight cerasin wax;

(b) heating the composition of (a) to a temperature above the melting point of the composition, causing the composition to melt;

(c) applying from about 100 to about 1,000,000 deposits of the melted composition per square inch to one or both sides of a tissue web; and (d) resolidifying the deposits of the melted composition.

26. The method according to claim 25, wherein the tissue product provides a cooling sensation when in contact with skin.

27. The method according to claim 25, wherein the composition has a melting temperature of from about 30° C. to about 70° C.

28. A soft tissue product having one or more tissue plies, wherein one or both outer surfaces of the product have solidified deposits having a composition comprising:
about 0.1 to 5 parts by weight of a silicone oil,
about 0.2 to 10 parts by weight of a $C_{1-18}$ alkyl ester of a fatty acid,
about 0.25 to 35 parts by weight purified mineral oil,
about 30 to 40 parts by weight fatty alcohol ethoxylate or fatty acid
ethoxylate having 1 to 200 moles EO, and
about 15 to 20 parts by weight of a fatty alcohol;
about 20 to 40 parts by weight dimethicone, 29. The soft tissue product according to claim 28, wherein the tissue product provides a cooling sensation upon contact with skin.

30. The soft tissue product according to claim 28, wherein the composition has a melting temperature of from about 30° C. to about 70° C.

31. The soft tissue product according to claim 27 wherein the composition comprises:
about 15 to 35 parts by weight mineral oil,
about 5 to 15 parts by weight of a mixture of cetyl acetate and acetylated lanolin alcohol,
about 15 to 25 parts by weight tridecyl neopentanoate, and
about 10 to 30 parts by weight cerasin wax.

32. A soft tissue product having one or more tissue plies, wherein one or both outer surfaces of the product have solidified deposits having a composition comprising:
about 2 parts by weight dimethicone,
about 4 parts by weight isopropyl palmitate,
about 34 parts by weight mineral oil,
about 35 parts by weight ceteareth-20, and
about 20 parts by weight cetyl alcohol.

33. The soft tissue product according to claim 32, wherein the tissue product provides a cooling sensation upon contact with skin.

34. The soft tissue product according to claim 32, wherein the composition has a melting temperature of from about 30° C. to about 70° C.

35. A composition for coating a tissue product, the composition comprising:
 about 20 to 40 parts by weight dimethicone,
 about 15 to 35 parts by weight mineral oil,
 about 5 to 15 parts by weight of a mixture of cetyl acetate and acetylated lanolin alcohol,
 about 15 to 25 parts by weight tridecyl neopentanoate, and
 about 10 to 30 parts by weight cerasin wax.

36. A composition for coating a tissue product, the composition comprising:
 about 2 parts by weight dimethicone,
 about 4 parts by weight isopropyl palmitate,
 about 34 parts by weight mineral oil,
 about 35 parts by weight ceteareth-20, and
 about 20 parts by weight cetyl alcohol.

\* \* \* \* \*